(12) United States Patent
Omura

(10) Patent No.: US 12,162,852 B2
(45) Date of Patent: Dec. 10, 2024

(54) LACTONE COMPOUND

(71) Applicant: FUJIFILM Corporation, Tokyo (JP)

(72) Inventor: Kazufumi Omura, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 18/047,654

(22) Filed: Oct. 19, 2022

(65) Prior Publication Data

US 2023/0141533 A1    May 11, 2023

(30) Foreign Application Priority Data

Oct. 22, 2021   (JP) ................................. 2021-172849

(51) Int. Cl.
*C07D 307/83*   (2006.01)

(52) U.S. Cl.
CPC .................................. *C07D 307/83* (2013.01)

(58) Field of Classification Search
CPC ........................... C07D 307/83; A61K 31/365
USPC ......................................... 549/307; 514/470
See application file for complete search history.

(56) References Cited

U.S. PATENT DOCUMENTS

| | | |
|---|---|---|
| 5,516,920 A | 5/1996 | Nesvadba et al. |
| 5,607,624 A | 3/1997 | Nesvadba et al. |
| 5,773,631 A | 6/1998 | Nesvadba et al. |
| 5,814,692 A | 9/1998 | Nesvadba et al. |
| 6,346,630 B1 | 2/2002 | Nesvadba et al. |
| 6,359,148 B1 | 3/2002 | Nesvadba et al. |

FOREIGN PATENT DOCUMENTS

| | | | | |
|---|---|---|---|---|
| DE | 443273 | * | 3/1995 | ........... C07D 307/83 |
| DE | 4432732 | * | 3/1995 | ........... C07D 307/83 |
| JP | H07165745 | | 6/1995 | |
| JP | H07233160 | | 9/1995 | |

OTHER PUBLICATIONS

US 5,955,619 A, 09/1999, Nesvadba et al. (withdrawn)
Tang, et. al., CCS Chemistry (2020), 2, 2245-2258. (Year: 2020).*
https://www.wiredchemist.com/data/hammett-sigma-constants; last accessed Jan. 27, 2024. (Year: 2024).*
Yang, et. al., Gaodeng Xuexiao Huaxue Xuebao (2011), 32(2), 286-291. (Year: 2011).*

* cited by examiner

*Primary Examiner* — Jeffrey H Murray
(74) *Attorney, Agent, or Firm* — JCIPRNET

(57) ABSTRACT

An object of the present invention is to provide a lactone compound having excellent water stability.
Provided is a lactone compound represented by Formula (I).

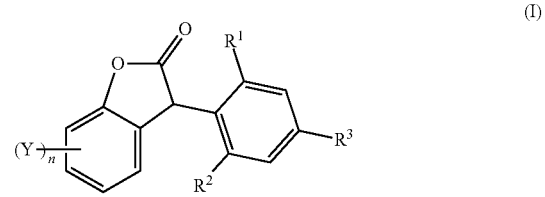

(I)

In Formula (I), $R^1$ and $R^2$ each independently represent a substituent which does not have a dissociative proton and has a Hammett's substituent constant σp value of −0.90 or more and −0.03 or less. $R^3$ represents a substituent which does not have a dissociative proton and has a Hammett's substituent constant σp value of −0.90 or more and −0.03 or less, or a hydrogen atom. Y represents a substituent and n represents an integer of 1 to 4. In a case where n is an integer of 2 to 4, a plurality of Y's may be the same substituent or substituents different from each other.

4 Claims, No Drawings

LACTONE COMPOUND

CROSS-REFERENCE TO RELATED APPLICATIONS

The present application claims priority under 35 U.S.C. § 119 to Japanese Patent Application No. 2021-172849, filed on Oct. 22, 2021. The above application is hereby expressly incorporated by reference, in its entirety, into the present application.

BACKGROUND OF THE INVENTION

1. Field of the Invention

The present invention relates to a novel lactone compound.

2. Description of the Related Art

3-Arylbenzofuranone, which is a kind of a lactone compound, has been known to be suitable as a stabilizer for an organic material susceptible to oxidation, heat, or photodecomposition (for example, see JP1995-233160A (JP-H07-233160A) and JP1995-165745A (JP-H07-165745A)).

SUMMARY OF THE INVENTION

The present inventor has studied on the lactone compound disclosed in JP1995-233160A (JP-H07-233160A) and JP1995-165745A (JP-H07-165745A), and has found that, since the lactone compound easily decomposes in a case of being brought into contact with water in a highly dispersed state, there is room for improvement in stability to water (hereinafter, abbreviated as "water stability").

An object of the present invention is to provide a lactone compound having excellent water stability.

As a result of intensive studies to achieve the above-described object, the present inventor has found that benzofuranone having a phenyl group with a specific substituent at a predetermined position has excellent water stability, and has completed the present invention.

That is, the present inventor has found that the above-described object can be achieved by adopting the following configurations.

[1] A lactone compound represented by Formula (I),

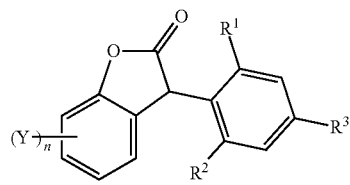
(I)

here, in Formula (I), $R^1$ and $R^2$ each independently represent a substituent which does not have a dissociative proton and has a Hammett's substituent constant σp value of −0.90 or more and −0.03 or less, $R^3$ represents a substituent which does not have a dissociative proton and has a Hammett's substituent constant σp value of −0.90 or more and −0.03 or less, or a hydrogen atom, Y represents a substituent and n represents an integer of 1 to 4, and in a case where n is an integer of 2 to 4, a plurality of Y's may be the same substituent or substituents different from each other.

[2] The lactone compound according to [1], in which $R^3$ in Formula (I) represents the substituent which does not have a dissociative proton and has a Hammett's substituent constant σp value of −0.90 or more and −0.03 or less.

[3] The lactone compound according to [1] or [2], in which $R^1$ and $R^2$ in Formula (I) each independently represent an alkyl group, an alkoxy group, an alkylamino group, an alkylsulfanyl group, or an allyl group.

[4] The lactone compound according to any one of [1] to [3], in which $R^1$ and $R^2$ in Formula (I) each independently represent an alkyl group or an alkoxy group.

[5] The lactone compound according to any one of [1] to [4], in which $R^1$ to $R^3$ in Formula (I) represent the same substituent.

[6] The lactone compound according to any one of [1] to [5], in which Y in Formula (I) represents a substituent having 3 or more carbon atoms.

[7] The lactone compound according to any one of [1] to [6], in which the lactone compound is represented by any of Formulae (1) to (4).

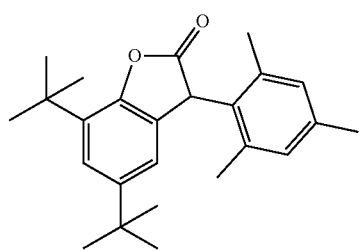
(1)

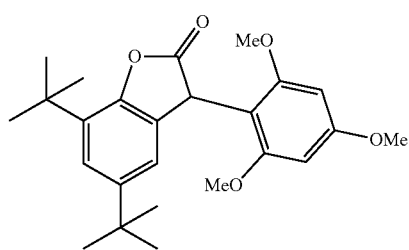
(2)

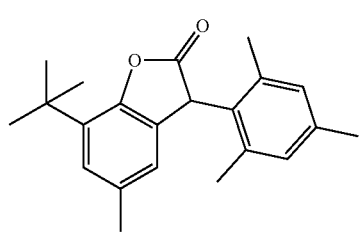
(3)

-continued

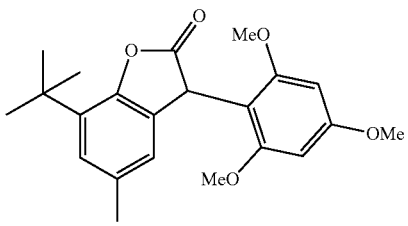

(4)

According to the present invention, it is possible to provide a lactone compound having excellent water stability.

DESCRIPTION OF THE PREFERRED EMBODIMENTS

Hereinafter, the present invention will be described in detail.

The description of configuration requirements described below may be made on the basis of representative embodiments of the present invention, but it should not be construed that the present invention is limited to those embodiments.

In the specification of the present application, the numerical range expressed by using "to" means a range including the numerical values before and after "to" as the lower limit value and the upper limit value.

Lactone Compound

A lactone compound according to an embodiment of the present invention is a lactone compound represented by Formula (I).

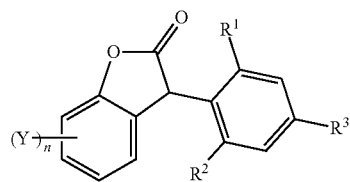

(I)

Here, in Formula (I), $R^1$ and $R^2$ each independently represent a substituent which does not have a dissociative proton and has a Hammett's substituent constant σp value of −0.90 or more and −0.03 or less.

In addition, $R^3$ represents a substituent which does not have a dissociative proton and has a Hammett's substituent constant σp value of −0.90 or more and −0.03 or less, or a hydrogen atom.

In addition, Y represents a substituent and n represents an integer of 1 to 4. In a case where n is an integer of 2 to 4, a plurality of Y's may be the same substituent or substituents different from each other.

In the present invention, water stability of the lactone compound represented by Formula (I) is good.

Although the details thereof are not clear, the present inventor has assumed as follows.

It is considered that there are two types of mechanisms for the water stability, which are different from each other depending on water stability over time without applied voltage and water stability under applied voltage.

First, the water stability over time without applied voltage will be described.

From the results of Comparative Examples 1 and 3 shown in Table 1 described later, in a case where a benzene ring at the 3-position of benzofuranone does not have substituents at the 2- and 6-positions of the benzene ring, it can be seen that the water stability over time is deteriorated. It is presumed that this cause is due to progress of hydrolysis of the lactone ring.

In addition, from the results of Comparative Example 2 shown in Table 1 described later, in a case where the benzene ring has substituents at the 3- and 5-positions even in a case where the benzene ring has substituents at the 2- and 6-positions, it can be seen that, although the water stability is slightly improved over that of Comparative Examples 1 and 3, the water stability is still deteriorated. It is presumed that this cause is due to that, although the progress of hydrolysis of the lactone ring can be suppressed, reducing power of the compound increases by making it easier to generate an H radical from the 3-position carbon atom of the lactone ring, and as a result, dimerization of the lactone ring is progressed.

Therefore, in the present invention, since the compound has substituents as $R^1$ and $R^2$ at the 2- and 6-positions of the benzene ring and does not have substituents at the 3- and 5-positions, it is considered that a planar structure of the benzofuranone and the benzene ring stably exists in a twisted position as shown below, and the progress of dimerization of the lactone ring is suppressed, thereby improving the water stability over time.

Next, the water stability under applied voltage will be described.

An O (oxygen) radical can be forcibly generated by applying a voltage to water.

Here, in order for 3-arylbenzofuranone to function as a stabilizer for an organic material susceptible to oxidation, heat, or photodecomposition, it is necessary to be stable against the O radical and to generate the H radical from the 3-position carbon atom of the lactone ring.

From the results of Examples 1 to 4 and Comparative Examples 4 and 5 shown in Table 2 described later, even in a case where a benzene ring at the 3-position of benzofuranone has substituents at the 2- and 6-positions of the benzene ring, in a case where the benzene ring has a substituent (for example, a hydroxyl group or the like) having a dissociative proton [hereinafter, abbreviated as a "dissociative substituent" in this paragraph"], it can be seen that the water stability against voltage is deteriorated. It is presumed that this is because the hydroxyl group on the benzene ring acts as phenol, and oxidative decomposition proceeds due to the reaction between the O radical derived from water and the phenol. That is, in a case where the benzene ring at the 3-position of benzofuranone has the dissociative substituents at the 2- and 6-positions or at other 3-, 4-, and 5-positions of the benzene ring, it is considered that the compound is not a lactone compound due to the progress of decomposition derived from the hydroxyl group, so that it is impossible to generate the H radical from the 3-position carbon atom of the lactone ring, and the function as a stabilizer is lost.

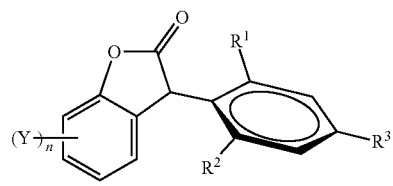

Hereinafter, $R^1$ to $R^3$, Y, and n in Formula (I) will be described in detail.

$R^1$ and $R^2$ in Formula (I) each independently represent a substituent which does not have a dissociative proton and has a Hammett's substituent constant σp value of −0.90 or more and −0.03 or less.

Here, the Hammett's substituent constant σp value will be described.

The Hammett's rule is an empirical rule advocated by L. P. Hammett in 1935 so as to quantitatively discuss the effect of substituent on the reaction or equilibrium of benzene derivatives and its propriety is widely admitted at present.

The substituent constant determined by the Hammett's rule includes a σp value and a σm value and these values can be found in a large number of general publications, and in the present invention, among σ values described in the literature "The Effect of Structure upon the Reactions of Organic Compounds. Benzene Derivatives" (J. Am. Chem. Soc. 1937, 59, 1, 96 to 103), the σ value (σp value) at the para position is used, and for substituents not specifically described in the literature, values calculated according to the calculation method described in the literature are used.

In addition, the "substituent which does not have a dissociative proton" is intended to exclude substituents having an active hydrogen, such as a hydroxyl group (—OH), an amino group (—NH$_2$, —NHR (R represents a monovalent organic group)), and a thiol group (—SH).

In the present invention, in the synthesis using the reaction of 3-hydroxybenzofuranone and benzene having a substituent (Friedel-Crafts reaction), from the reason that reactivity is good, it is preferable that $R^1$ and $R^2$ in Formula (I) each independently represent a substituent which does not have a dissociative proton and has a Hammett's substituent constant σp value of −0.20 or more and −0.03 or less.

In Formula (I), as the substituent represented by $R^1$ and $R^2$, from the reason that the water stability (particularly, the water stability over time) is further improved, an alkyl group, an alkoxy group, an alkylamino group, an alkylsulfanyl group, or an allyl group is preferable, and an alkyl group or an alkoxy group is more preferable.

As the alkyl group, for example, a linear, branched, or cyclic alkyl group having 1 to 18 carbon atoms is preferable, an alkyl group having 1 to 8 carbon atoms (for example, a methyl group, an ethyl group, a propyl group, an isopropyl group, an n-butyl group, an isobutyl group, a sec-butyl group, a tert-butyl group, a cyclohexyl group, and the like) is more preferable, an alkyl group having 1 to 4 carbon atoms is still more preferable, and a methyl group, an ethyl group, or an isopropyl group is particularly preferable.

As the alkoxy group, for example, an alkoxy group having 1 to 18 carbon atoms is preferable, an alkoxy group having 1 to 8 carbon atoms (for example, a methoxy group, an ethoxy group, an n-butoxy group, a methoxyethoxy group, and the like) is more preferable, an alkoxy group having 1 to 4 carbon atoms is still more preferable, and a methoxy group or an ethoxy group is particularly preferable.

As the alkylamino group, for example, a dialkylamino group or a diarylamino group substituted with a linear, branched, or cyclic alkyl group having 1 to 18 carbon atoms is preferable, a dialkylamino group is more preferable, and a dimethylamino group is still more preferable.

As the alkylsulfanyl group, an alkylsulfanyl group substituted with a linear, branched, or cyclic alkyl group having 1 to 18 carbon atoms is preferable, and for example, a methylsulfanyl group, an ethylsulfanyl group, a propylsulfanyl group, an isopropylsulfanyl group, an n-butylsulfanyl group, an isobutylsulfanyl group, a sec-butylsulfanyl group, a tert-butylsulfanyl group, or a cyclohexylsulfanyl group is preferable, a methylsulfanyl group, an ethylsulfanyl group, a propylsulfanyl group, or an isopropylsulfanyl group is more preferable, and a methylsulfanyl group or an ethylsulfanyl group is still more preferable.

Examples of the allyl group include a 2-propenyl group.

$R^3$ in Formula (I) represents a substituent which does not have a dissociative proton and has a Hammett's substituent constant σp value of −0.90 or more and −0.03 or less, or a hydrogen atom, and in the synthesis using the reaction of 3-hydroxybenzofuranone and benzene having a substituent (Friedel-Crafts reaction), from the reason that reactivity is good, the above-described substituent is preferable.

Here, examples of the above-described substituent include the same substituents as those described in $R^1$ and $R^2$ in Formula (I), and among them, an alkyl group or an alkoxy group is preferable.

In the present invention, in the synthesis using the reaction of 3-hydroxybenzofuranone and benzene having a substituent (Friedel-Crafts reaction), from the reason that isomers are not generated, it is preferable that $R^1$ to $R^3$ in Formula (I) represent the same substituent.

In Formula (I), as the substituent represented by Y, for example, any one selected from the substituent group Z shown below can be used.

Substituent group Z:
an alkyl group (preferably an alkyl group having 1 to 30 carbon atoms, more preferably an alkyl group having 1 to 20 carbon atoms, and particularly preferably an alkyl group having 1 to 10 carbon atoms; for example, methyl, ethyl, Iso-propyl, tert-butyl, n-octyl, n-decyl, and n-hexadecyl);

a cycloalkyl group (preferably a cycloalkyl group having 3 to 30 carbon atoms, more preferably a cycloalkyl group having 3 to 20 carbon atoms, and particularly preferably a cycloalkyl group having 3 to 10 carbon atoms; examples thereof include cyclopropyl, cyclopentyl, and cyclohexyl);

an alkenyl group (preferably an alkenyl group having 2 to 30 carbon atoms, more preferably an alkenyl group having 2 to 20 carbon atoms, and particularly preferably an alkenyl group having 2 to 10 carbon atoms; examples thereof include vinyl, allyl, 2-butenyl, and 3-pentenyl);

an alkynyl group (preferably an alkynyl group having 2 to 30 carbon atoms, more preferably an alkynyl group having 2 to 20 carbon atoms, and particularly preferably an alkynyl group having 2 to 10 carbon atoms; examples thereof include propargyl and 3-pentynyl);

an aryl group (preferably an aryl group having 6 to 30 carbon atoms, more preferably an aryl group having 6 to 20 carbon atoms, and particularly preferably an aryl group having 6 to 12 carbon atoms; examples thereof include phenyl, p-methylphenyl, naphthyl, and anthranyl);

an amino group (preferably an amino group having 0 to 30 carbon atoms, more preferably an amino group having 0 to 20 carbon atoms, and particularly preferably an amino group having 0 to 10 carbon atoms; examples thereof include amino, methylamino, dimethylamino, diethylamino, dibenzylamino, diphenylamino, and ditolylamino);

an alkoxy group (preferably an alkoxy group having 1 to 30 carbon atoms, more preferably an alkoxy group having 1 to 20 carbon atoms, and particularly preferably an alkoxy group having 1 to 10 carbon atoms; examples thereof include methoxy, ethoxy, butoxy, and 2-ethylhexyloxy);

an aryloxy group (preferably an aryloxy group having 6 to 30 carbon atoms, more preferably an aryloxy group having 6 to 20 carbon atoms, and particularly preferably an aryloxy group having 6 to 12 carbon atoms; examples thereof include phenyloxy, 1-naphthyloxy, and 2-naphthyloxy);

a heterocyclic oxy group (preferably a heterocyclic oxy group having 1 to 30 carbon atoms, more preferably a heterocyclic oxy group having 1 to 20 carbon atoms, and particularly preferably a heterocyclic oxy group having 1 to 12 carbon atoms; examples thereof include pyridyloxy, pyraziloxy, pyrimidyloxy, and quinolyloxy);

an acyl group (preferably an acyl group having 1 to 30 carbon atoms, more preferably an acyl group having 1 to 20 carbon atoms, and particularly preferably an acyl group having 1 to 12 carbon atoms; examples thereof include acetyl, benzoyl, formyl, and pivaloyl);

an alkoxycarbonyl group (preferably an alkoxycarbonyl group having 2 to 30 carbon atoms, more preferably an alkoxycarbonyl group having 2 to 20 carbon atoms, and particularly preferably an alkoxycarbonyl group having 2 to 12 carbon atoms; examples thereof include methoxycarbonyl and ethoxycarbonyl);

an aryloxycarbonyl group (preferably an aryloxycarbonyl group having 7 to 30 carbon atoms, more preferably an aryloxycarbonyl group having 7 to 20 carbon atoms, and particularly preferably an aryloxycarbonyl group having 7 to 12 carbon atoms; examples thereof include phenyloxycarbonyl);

an acyloxy group (preferably an acyloxy group having 2 to 30 carbon atoms, more preferably an acyloxy group having 2 to 20 carbon atoms, and particularly preferably an acyloxy group having 2 to 10 carbon atoms; examples thereof include acetoxy and benzoyloxy);

an acylamino group (preferably an acylamino group having 2 to 30 carbon atoms, more preferably an acylamino group having 2 to 20 carbon atoms, and particularly preferably an acylamino group having 2 to 10 carbon atoms; examples thereof include acetylamino and benzoylamino);

an alkoxycarbonylamino group (preferably an alkoxycarbonylamino group having 2 to 30 carbon atoms, more preferably an alkoxycarbonylamino group having 2 to 20 carbon atoms, and particularly preferably an alkoxycarbonylamino group having 2 to 12 carbon atoms; examples thereof include methoxycarbonylamino);

an aryloxycarbonylamino group (preferably an aryloxycarbonylamino group having 7 to 30 carbon atoms, more preferably an aryloxycarbonylamino group having 7 to 20 carbon atoms, and particularly preferably an aryloxycarbonylamino group having 7 to 12 carbon atoms; examples thereof include phenyloxycarbonylamino);

a sulfonylamino group (preferably a sulfonylamino group having 1 to 30 carbon atoms, more preferably a sulfonylamino group having 1 to 20 carbon atoms, and particularly preferably a sulfonylamino group having 1 to 12 carbon atoms; examples thereof include methanesulfonylamino and benzenesulfonylamino);

a sulfamoyl group (preferably a sulfamoyl group having 0 to 30 carbon atoms, more preferably a sulfamoyl group having 0 to 20 carbon atoms, and particularly preferably a sulfamoyl group having 0 to 12 carbon atoms; examples thereof include sulfamoyl, methylsulfamoyl, dimethylsulfamoyl, and phenylsulfamoyl);

a carbamoyl group (preferably a carbamoyl group having 1 to 30 carbon atoms, more preferably a carbamoyl group having 1 to 20 carbon atoms, and particularly preferably a carbamoyl group having 1 to 12 carbon atoms; examples thereof include carbamoyl, methylcarbamoyl, diethylcarbamoyl, and phenylcarbamoyl);

an alkylthio group (preferably an alkylthio group having 1 to 30 carbon atoms, more preferably an alkylthio group having 1 to 20 carbon atoms, and particularly preferably an alkylthio group having 1 to 12 carbon atoms; examples thereof include methylthio and ethylthio);

an arylthio group (preferably an arylthio group having 6 to 30 carbon atoms, more preferably an arylthio group having 6 to 20 carbon atoms, and particularly preferably an arylthio group having 6 to 12 carbon atoms; examples thereof include phenylthio);

a heterocyclic thio group (preferably a heterocyclic thio group having 1 to 30 carbon atoms, more preferably a heterocyclic thio group having 1 to 20 carbon atoms, and particularly preferably a heterocyclic thio group having 1 to 12 carbon atoms; examples thereof include pyridylthio, 2-benzimizolylthio, 2-benzoxazolylthio, and 2-benzthiazolylthio); [0024] a sulfonyl group (preferably a sulfonyl group having 1 to 30 carbon atoms, more preferably a sulfonyl group having 1 to 20 carbon atoms, and particularly preferably a sulfonyl group having 1 to 12 carbon atoms; examples thereof include mesyl and tosyl);

a sulfinyl group (preferably a sulfinyl group having 1 to 30 carbon atoms, more preferably a sulfinyl group having 1 to 20 carbon atoms, and particularly preferably a sulfinyl group having 1 to 12 carbon atoms; examples thereof include methanesulfinyl and benzenesulfinyl);

an ureido group (preferably an ureido group having 1 to 30 carbon atoms, more preferably an ureido group having 1 to 20 carbon atoms, and particularly preferably an ureido group having 1 to 12 carbon atoms; examples thereof include ureido, methylureido, and phenylureido);

a phosphoric acid amide group (preferably a phosphoric acid amide group having 1 to 30 carbon atoms, more preferably a phosphoric acid amide group having 1 to 20 carbon atoms, and particularly preferably a phosphoric acid amide group having 1 to 12 carbon atoms; examples thereof include diethylphosphoric acid amide and phenylphosphoric acid amide);

a hydroxy group; a mercapto group;

a halogen atom (for example, a fluorine atom, a chlorine atom, a bromine atom, and an iodine atom, and a fluorine atom is more preferable);

a cyano group; a sulfo group; a carboxyl group; an oxo group; a nitro group; a hydroxamic acid group; a sulfino group; a hydradino group; an imino group;

a heterocyclic group (preferably a heterocyclic group having 1 to 30 carbon atoms and more preferably a heterocyclic group having 1 to 12 carbon atoms; examples of the heteroatom include a nitrogen atom, an oxygen atom, and a sulfur atom; specific examples thereof include imidazolyl, pyridyl, quinolyl, furyl, thienyl, piperidyl, morpholino, benzoxazolyl, benzimidazolyl, benzthiazolyl, carbazolyl group, and azepinyl group);

a silyl group (preferably a silyl group having 3 to 40 carbon atoms, more preferably a silyl group having 3 to 30 carbon atoms, and particularly preferably a silyl group having 3 to 24 carbon atoms; examples thereof include trimethylsilyl and triphenylsilyl); and a silyloxy group (preferably a silyloxy group having 3 to 40 carbon atoms, more preferably a silyloxy group having 3 to 30 carbon atoms, and particularly preferably a silyloxy group having 3 to 24 carbon atoms; examples thereof include trimethylsilyloxy and triphenylsilyloxy).

These substituents may be further substituted with any one or more substituents selected from the substituent group Z.

In the present invention, in the synthesis using the reaction of phenol and glyoxylic acid (Friedel-Crafts reaction), from the reason that reactivity for forming a lactone ring including the substituent Y is good, it is preferable that Y in Formula (I) is a substituent having a Hammett's substituent constant σp value of −0.90 or more and −0.03 or less.

Here, examples of the above-described substituent include the same substituents as those described in $R^1$ and $R^2$ in Formula (I), and among them, an alkyl group is preferable.

In addition, in the present invention, in the synthesis using the reaction of phenol and glyoxylic acid (Friedel-Crafts reaction), from the reason that reactivity for forming a lactone ring including the substituent Y is good, it is preferable that Y in Formula (I) represents a substituent having 3 or more carbon atoms, more preferable that Y in Formula (I) represents a substituent having 3 to 30 carbon atoms, and specifically, a tert-butyl group is more preferable.

The "Y in Formula (I) represents a substituent having 3 or more carbon atoms" means that, in a case where a plurality of Y's in Formula (I) are present, all Y's have the substituent having 3 or more carbon atoms.

In Formula (1) represents an integer of 1 to 4, and 1 or 2 is preferable. In a case where n is an integer of 2 to 4, a plurality of Y's may be the same substituent or substituents different from each other.

Specific examples of the lactone compound represented by Formula (I) include compounds (1) to (4) represented by Formulae (1) to (4).

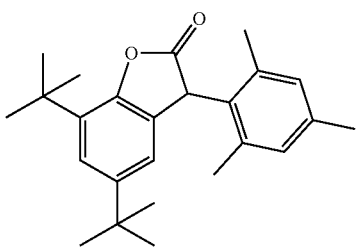

(1)

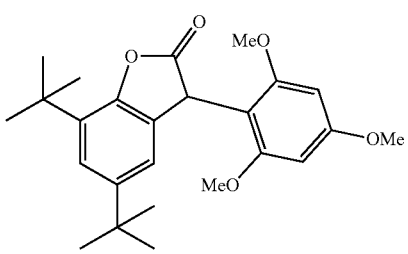

(2)

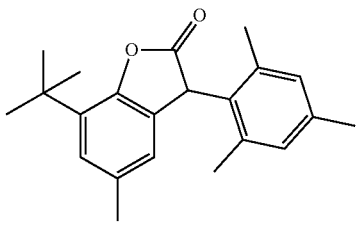

(3)

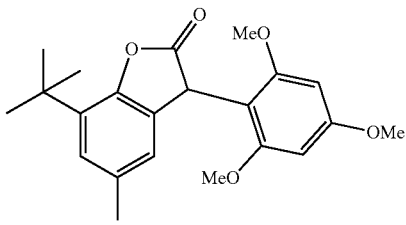

(4)

Polymer Compound

The lactone compound according to the embodiment of the present invention can be used as a stabilizer for a polymer compound.

Here, the polymer compound is not particularly limited as long as it corresponds to the organic material susceptible to oxidation, heat, or photodecomposition, and may be any of a water-soluble polymer compound or a water-insoluble polymer compound.

The water-soluble polymer compound is not particularly limited, and a known compound can be used. Specific examples thereof include proteins such as gelatin, casein, and albumin, polysaccharides such as starch and dextrin, cellulose and a derivative thereof (for example, carboxyl methyl cellulose, hydroxyl propyl cellulose, methyl cellulose, and the like), alginic acid, carrageenan, guar gum, xanthan gum, fucoidan, chitosan, hyaluronic acid, polyethylene oxide, polyvinyl alcohol, polyvinylpyrrolidone, polyvinyl methyl ether, polyacrylamide, polyethyleneimine, polyallylamine, polyvinylamine, polylysine, polyacrylic acid, and a graft-polymerized polymer thereof. In addition, a compound modified by a known method, such as succinated gelatin, can also be used.

The water-insoluble polymer compound is not particularly limited, and a known homopolymer or copolymer can be used.

Examples of the homopolymer include polymers such as vinyl acetate, vinyl chloride, styrene, methyl acrylate, butyl acrylate, methacrylonitrile, butadiene, and isoprene.

Examples of the copolymer include an ethylene/butadiene copolymer, a styrene/butadiene copolymer, a styrene/p-methoxystyrene copolymer, a styrene/vinyl acetate copolymer, a vinyl acetate/vinyl chloride copolymer, a vinyl acetate/diethyl maleate copolymer, a methyl methacrylate/acrylonitrile copolymer, a methyl methacrylate/butadiene copolymer, a methyl methacrylate/styrene copolymer, a methyl methacrylate/vinyl acetate copolymer, a methyl methacrylate/vinylidene chloride copolymer, a methyl acrylate/acrylonitrile copolymer, a methyl acrylate/butadiene copolymer, a methyl acrylate/styrene copolymer, a methyl acrylate/vinyl acetate copolymer, an acrylic acid/butyl acrylate copolymer, a methyl acrylate/vinyl chloride copolymer, a butyl acrylate/styrene copolymer, polyester, polycarbonate, and various urethanes.

A content of such a polymer compound is not particularly limited, but with respect to 100 parts by mass of the above-described lactone compound according to the embodiment of the present invention, is preferably 1,000 to 10,000,000 parts by mass, more preferably 100,000 to 10,000,000 parts by mass, and still more preferably 200,000 to 2,000,000 parts by mass.

In addition, with respect to 100 parts by mass of the polymer compound, a content of the above-described lactone compound according to the embodiment of the present invention is preferably 0.001 to 10 parts by mass, more preferably 0.001 to 0.1 parts by mass, and still more preferably 0.005 to 0.05 parts by mass.

In addition, in a case where the lactone compound according to the embodiment of the present invention is used as a stabilizer or the like, co-stabilizers described in paragraphs [0180] to [0212] of JP1995-233160A (JP-H07-233160A) and paragraphs [0199] to [0222] of JP2019-014826A can be used in combination.

EXAMPLES

Hereinafter, the present invention will be described in more detail with reference to examples. Materials, amounts used, ratios, treatment contents, treatment procedures, and the like shown in the following examples can be appropriately changed without departing from the spirit of the present invention. Accordingly, the scope of the present invention is not limited to the following Examples.

Example 1

Synthesis of Compound (1)

21.3 parts by mass of 2,4-di-tert-butylphenol (manufactured by Tokyo Chemical Industry Co., Ltd.), 10.4 parts by mass of glyoxylic acid monohydrate (manufactured by FUJIFILM Wako Pure Chemical Corporation), 0.051 parts by mass of p-toluenesulfonic acid monohydrate (manufactured by Tokyo Chemical Industry Co., Ltd.), and 40 parts by mass of 1,2-dichloroethane (manufactured by Tokyo Chemical Industry Co., Ltd.) were weighed in a flask.

Next, the weighed flask was placed in an oil bath at 105° C., and while distilling off the distillate using a Dean Stark tube, heating was continued until the internal temperature reached 86° C. by adding the same amount of 1,2-dichloroethane as the amount of distillation.

Next, the oil bath was heated to 120° C., and the resulting mixture was concentrated so that the residual amount of 1,2-dichloroethane was less than 10 parts by mass. Thereafter, the reaction solution was cooled to room temperature (23° C.), 100 parts by mass of hexane and 100 parts by mass of water were added thereto, and the mixture was stirred. Thereafter, the hexane layer was recovered, 100 parts by mass of saturated saline was added thereto, and the mixture was stirred. Thereafter, the hexane layer was recovered, 1 part by mass of magnesium sulfate (manufactured by FUJIFILM Wako Pure Chemical Corporation) was added thereto, and the mixture was dried for 1 hour.

Next, the magnesium sulfate was filtered off and the hexane layer was concentrated to dryness using an evaporator to obtain 27.0 parts by mass of a brown viscous substance (1) containing a compound (1a) represented by Formula (1a).

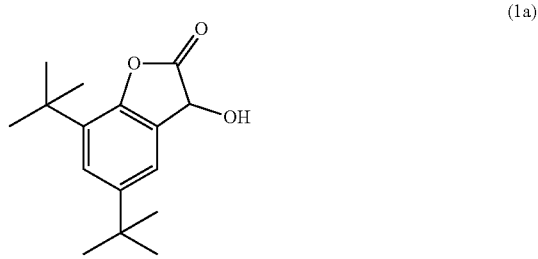 [SMILES: CC(C)(C)c1cc2c(c(C(C)(C)C)c1)OC(=O)C2O]

Next, 13.6 parts by mass of mesitylene (manufactured by Tokyo Chemical Industry Co., Ltd.), 39.5 parts by mass of tin (IV) chloride pentahydrate (manufactured by Tokyo Chemical Industry Co., Ltd.), and 85 parts by mass of 1,2-dichloroethane were weighed, and the mixture was refluxed for 4 hours using an oil bath at 105° C.

Next, after distilling off 46 parts by mass of the 1,2-dichloroethane, the reaction solution was cooled to room temperature (23° C.), and 460 parts by mass of ethyl acetate and 460 parts by mass of water were added thereto. Thereafter, the ethyl acetate layer was recovered, 460 parts by mass of saturated saline was added thereto, and the mixture was stirred. Thereafter, the ethyl acetate layer was recovered, and using 460 parts by mass of saturated saline, liquid separation purification was repeated until the pH of the saturated saline layer was to be 6. Thereafter, the ethyl acetate layer was recovered, 1 part by mass of magnesium sulfate was added thereto, and the mixture was dried for 1 hour.

Next, the magnesium sulfate was filtered off through Celite, and the ethyl acetate layer was concentrated to dryness using an evaporator. Thereafter, 115 parts by mass of methanol was added to the dry matter, and the mixture was stirred at room temperature (23° C.) for 24 hours to precipitate crystals.

Next, the crystals were filtered and dried, and then column chromatography was performed using hexane alone and an eluent of hexane:ethyl acetate=19:1 to obtain a compound (1) represented by Formula (1) described above (recovery amount: 22.5 parts by mass, yield: 60%, purity: 99%). The purity is a value calculated from a measurement result of a high-performance liquid chromatography (HPLC), and is also abbreviated as an "HPLC purity" below.

[1]H-nuclear magnetic resonance (NMR) data of the obtained compound (1) and assignments thereof are shown below. In the compound (1), the substituent constant σp values of substituents corresponding to $R^1$, $R^2$, and $R^3$ in Formula (I) described above were all −0.170.

$^1$H-NMR (CDCl$_3$) δ (ppm)=1.24 (9H, s), 1.44 (9H, s), 1.73 (3H, s), 2.28 (3H, s), 2.52 (3H, s), 5.24 (1H, s), 6.79 (1H, s), 6.81 (1H, s), 6.97 (1H, s), 7.27 (1H, s)

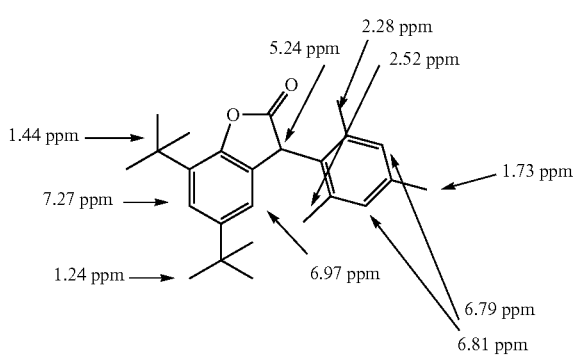 [SMILES: Cc1cc(C)c(C2C(=O)Oc3c2cc(C(C)(C)C)cc3C(C)(C)C)c(C)c1]

Example 2

Synthesis of Compound (2)

A compound (2) represented by Formula (2) described above was obtained by the same method as in the synthesis of the compound (1), except that 13.6 parts by mass of mesitylene was changed to 19.2 parts by mass of 1,3,5-trimethoxybenzene (manufactured by Tokyo Chemical Industry Co., Ltd.).

$^1$H-NMR data of the obtained compound (2) and assignments thereof are shown below. In the compound (2), the substituent constant σp values of substituents corresponding to $R^1$, $R^2$, and $R^3$ in Formula (I) described above were all −0.268.

$^1$H-NMR (CDCl$_3$) δ (ppm)=1.24 (9H, s), 1.44 (9H, s), 3.51 (3H, s), 3.81 (3H, s), 3.91 (3H, s), 5.24 (11H, s), 6.05 (1H, d), 6.22 (1H, d), 6.81 (1H, s), 7.19 (1H, s)

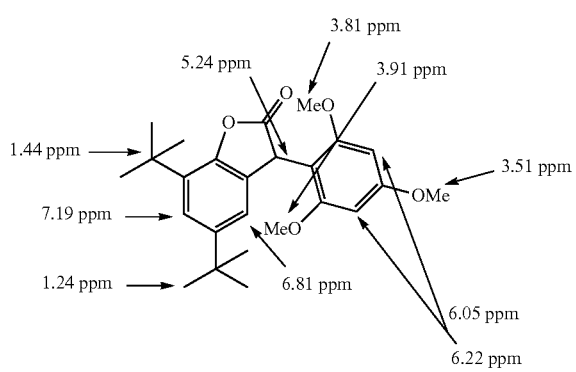 [SMILES: COc1cc(OC)c(C2C(=O)Oc3c2cc(C(C)(C)C)cc3C(C)(C)C)c(OC)c1]

Example 3

Synthesis of Compound (3a)

100 parts by mass of 2-tert-butyl-p-cresol (manufactured by Tokyo Chemical Industry Co., Ltd.), 61.6 parts by mass of glyoxylic acid monohydrate (manufactured by FUJIFILM Wako Pure Chemical Corporation), 0.30 parts by mass of p-toluenesulfonic acid monohydrate (manufactured by Tokyo Chemical Industry Co., Ltd.), and 150 parts by mass of 1,2-dichloroethane (manufactured by Tokyo Chemical Industry Co., Ltd.) were weighed in a flask.

Next, the weighed flask was placed in an oil bath at 105° C., and while distilling off the distillate using a Dean Stark tube, heating was continued until the internal temperature reached 86° C. by adding the same amount of 1,2-dichloroethane as the amount of distillation.

Next, the oil bath was heated to 120° C., and the resulting mixture was concentrated so that the residual amount of 1,2-dichloroethane was 75 parts by mass. Thereafter, the reaction solution was cooled to 40° C., 250 parts by mass of hexane and 250 parts by mass of water were added thereto, and the mixture was stirred. Thereafter, the hexane layer was recovered, 250 parts by mass of saturated saline was added thereto, and the mixture was stirred. Thereafter, the hexane layer was recovered, cooled to an internal temperature of 5° C. or lower using an ice-water bath, and stirred for 1 hour to precipitate crystals.

Next, the crystals were filtered and washed with 10 parts by mass of hexane. Thereafter, the crystals were added to 250 parts by mass of methanol, and suspension stirring was carried out at 5° C. or lower for 1 hour. Thereafter, the crystals were filtered off to obtain a white compound (3a) represented by Formula (3a) (recovery amount: 67.1 parts by mass, yield: 50%).

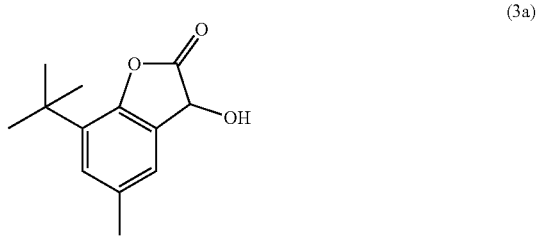 [SMILES: Cc1cc2c(c(C(C)(C)C)c1)OC(=O)C2O]

(3a)

Synthesis of Compound (3)

A compound (3) was obtained by the same method as in the synthesis of the compound (1), except that 27.0 parts by mass of the viscous substance (1) containing the compound (1a) was changed to 22.6 parts by mass of the compound (3a) synthesized above.

$^1$H-NMR data of the obtained compound (3) and assignments thereof are shown below. In the compound (3), the substituent constant σp values of substituents corresponding to $R^1$, $R^2$, and $R^3$ in Formula (I) described above were all −0.170.

$^1$H-NMR (CDCl$_3$) δ (ppm)=1.42 (9H, s), 1.75 (3H, s), 2.25 (3H, s), 2.27 (3H, s), 2.50 (3H, s), 5.22 (1H, s), 6.62 (1H, s), 6.79 (1H, s), 6.97 (1H, s), 7.03 (1H, s)

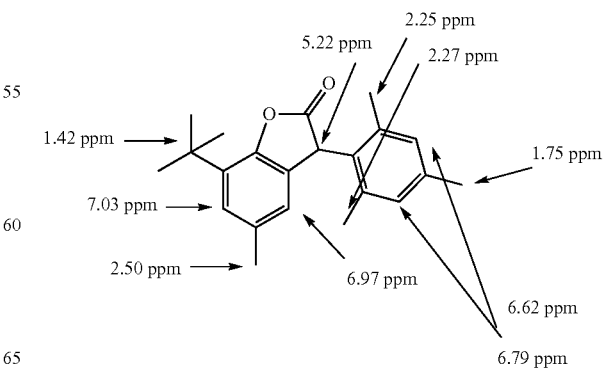

Example 4

Synthesis of Compound (4)

A compound (4) represented by Formula (4) described above was obtained by the same method as in the synthesis of the compound (3), except that 13.6 parts by mass of mesitylene was changed to 19.2 parts by mass of 1,3,5-trimethoxybenzene (manufactured by Tokyo Chemical Industry Co., Ltd.).

$^1$H-NMR data of the obtained compound (4) and assignments thereof are shown below. In the compound (4), the substituent constant σp values of substituents corresponding to $R^1$, $R^2$, and $R^3$ in Formula (I) described above were all −0.268.

$^1$H-NMR (CDCl$_3$) S (ppm)=1.43 (9H, s), 2.24 (3H, s), 3.53 (3H, s), 3.80 (3H, s), 3.90 (3H, s), 5.24 (1H, s), 6.04 (1H s), 6.22 (1H, s), 6.64 (1H, s), 6.96 (1H, s)

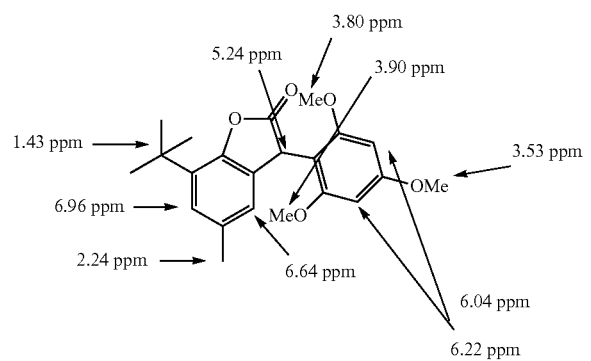 [SMILES: COc1cc(OC)c(C2C(=O)Oc3c2cc(C)cc3C(C)(C)C)c(OC)c1]

Comparative Example 1

Synthesis of Compound (5)

A compound (5) represented by Formula (5) was obtained by the same method as in the synthesis of the compound (1), except that 13.6 parts by mass of mesitylene was changed to 12.0 parts by mass of xylene (manufactured by Tokyo Chemical Industry Co., Ltd.).

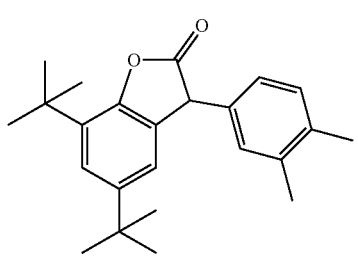

(5)

Comparative Example 2

Synthesis of Compound (6)

A compound (6) represented by Formula (6) was obtained by the same method as in the synthesis of the compound (1), except that 13.6 parts by mass of mesitylene was changed to 14.3 parts by mass of pentamethylbenzene (manufactured by Tokyo Chemical Industry Co., Ltd.).

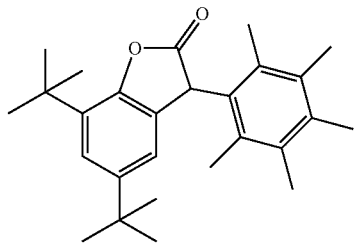

(6)

Comparative Example 3

Synthesis of Compound (7)

A compound (7) represented by Formula (7) was obtained by the same method as in the synthesis of the compound (1), except that 13.6 parts by mass of mesitylene was changed to 23.3 parts by mass of n-octylphenyl ether (manufactured by Tokyo Chemical Industry Co., Ltd.).

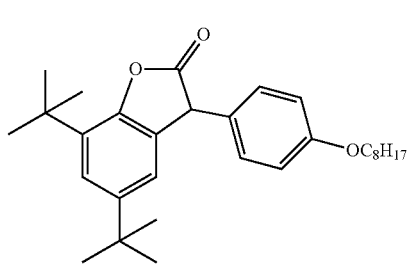

(7)

Comparative Example 4

Synthesis of Compound (8)

27.0 parts by mass of the viscous substance (1) containing the compound (1a) and 9.07 parts by mass of 4,6-di-tert-butyl-m-cresol were dissolved in 135 parts by mass of acetic acid.

Next, 27.0 parts by mass of sulfuric acid was added dropwise thereto over 30 minutes, the mixture was stirred at 30° C. for 24 hours, and the generated precipitate was filtered off.

Next, 300 parts by mass of ethyl acetate and 300 parts by mass of water were added to the filtered precipitate, the ethyl acetate layer was recovered, 300 parts by mass of saturated saline was added thereto, and the mixture was stirred. Thereafter, the ethyl acetate layer was recovered, and using 300 parts by mass of saturated saline, liquid separation purification was repeated until the pH of the saturated saline layer was to be 6.

Next, the ethyl acetate layer was recovered, 1 part by mass of magnesium sulfate was added thereto, and the mixture was dried for 1 hour.

Next, the magnesium sulfate was filtered off through Celite, and the ethyl acetate layer was concentrated to dryness using an evaporator to obtain a compound (8) represented by Formula (8).

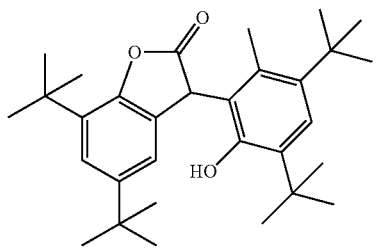

(8)

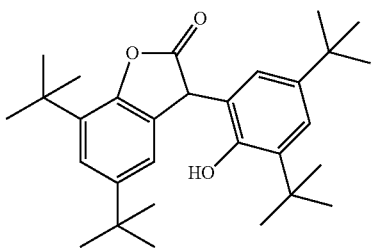 [SMILES: CC(C)(C)c1cc(C2C(=O)Oc3c2cc(C(C)(C)C)cc3C(C)(C)C)c(O)c(C(C)(C)C)c1]

(9)

Comparative Example 5

Synthesis of Compound (9)

20.0 parts by mass of 2,4-di-tert-butyl-phenol and 5.4 parts by mass of glyoxylic acid monohydrate were dissolved in 100 parts by mass of acetic acid.

Next, 20.0 parts by mass of sulfuric acid was added dropwise thereto over 30 minutes, the mixture was stirred at 30° C. for 24 hours, and the generated precipitate was filtered off.

Next, 300 parts by mass of ethyl acetate and 300 parts by mass of water were added to the filtered precipitate, the ethyl acetate layer was recovered, 300 parts by mass of saturated saline was added thereto, and the mixture was stirred. Thereafter, the ethyl acetate layer was recovered, and using 300 parts by mass of saturated saline, liquid separation purification was repeated until the pH of the saturated saline layer was to be 6.

Next, the ethyl acetate layer was recovered, 1 part by mass of magnesium sulfate was added thereto, and the mixture was dried for 1 hour.

Next, the magnesium sulfate was filtered off through Celite, and the ethyl acetate layer was concentrated to dryness using an evaporator to obtain a compound (9) represented by Formula (9).

Evaluation

Water stability of each of the compounds (1) to (9) synthesized in Examples and Comparative Examples was evaluated by the methods shown below.

Water Stability Over Time without Applied Voltage

To 1.0 part by mass of each of the compounds (1) to (9) synthesized in Examples and Comparative Examples, 1000 parts by mass of NIKKOL HCO-40 (Nikko Chemicals Co., Ltd.) and 10000 parts by mass of acetone were mixed.

Next, after removing the acetone using an evaporator at a temperature of 40° C., 10000 parts of water was added thereto to prepare a uniform mixed solution 1. The mixed solution 1 was allowed to stand at 25° C. for 24 hours.

Immediately after the preparation of the mixed solution 1 and after allowing the mixed solution 1 to stand for 24 hours, an HPLC measurement was carried out under the following analysis conditions, and a residual rate in the water stability test over time was calculated using the following expression. The results are shown in Table 1 below.

(Area value after standing for 24 hours)÷(Area value immediately after preparation)×100=Residual rate (%)

HPLC analysis conditions
SCL-10AVP manufactured by Shimadzu Corporation
Column: ODS-80™
Eluent: single eluent prepared by adding 0.2% by volume of each of acetic acid and triethylamine to a mixed solution obtained by mixing tetrahydrofuran (THF) and water at a ratio of 60:40
Flow rate: 1 ml/min
Column oven: 40° C.

Table 1

| | Example 1 Compound (1) | Example 2 Compound (2) | Example 3 Compound (3) |
|---|---|---|---|
| Structural Formula | | | |
| Residual rate (%) | 100 | 95 | 90 |

Table 1-continued

| | Example 4<br>Compound (4) | Comparative<br>Example 1<br>Compound (5) | Comparative<br>Example 2<br>Compound (6) |
|---|---|---|---|
| Structural<br>Formula | (structure) | (structure) | (structure) |
| Residual<br>rate (%) | 95 | 0 | 10 |

| | Comparative<br>Example 3<br>Compound (7) | Comparative<br>Example 4<br>Compound (8) | Comparative<br>Example 5<br>Compound (9) |
|---|---|---|---|
| Structural<br>Formula | (structure) | (structure) | (structure) |
| Residual<br>rate (%) | 0 | 0 | 0 |

From the results shown in Table 1, it was found that all of the compounds (5) to (9), which do not correspond to the lactone compound represented by Formula (I) described above, had a low residual rate and were deteriorated in water stability over time (Comparative Examples 1 to 5).

On the other hand, it was found that all of the compounds (1) to (4), which correspond to the lactone compound represented by Formula (I) described above, had a high residual rate and were excellent in water stability over time (Examples 1 to 4).

In addition, from the comparison between Examples 1 and 3, it was found that, in a case where Y in Formula (I) described above was a substituent having 3 or more carbon atoms, the water stability over time was further improved.

Water Stability Under Applied Voltage

Water stability against voltage of each of the compounds (1) to (9) synthesized in Examples and Comparative Examples was evaluated by the measurement shown below.

Analysis conditions
660A manufactured by ALS
Measurement: square wave voltammetry (SWV)
Action electrode: gold electrode
Counter electrode: platinum black electrode
Reference electrode: Ag wire
Supporting electrolyte: tetrabutylammonium hexafluorophosphate (manufactured by FUJIFILM Wako Pure Chemical Corporation)
Reference substance: ferrocene Measurement Conditions The compound (1) was adjusted to a concentration of 0.5 mM using a mixed solvent of THF:water=90:10, and nitrogen bubbling was carried out for 10 minutes to produce a measurement sample.

Next, a measurement was performed under the above-described analysis conditions to observe an oxidation potential. Since the solvent of THF was oxidized at 1.3 V, it was determined that there was no oxidation potential in a case of being more stable than 1.3 V.

Oxidation potentials of the compounds (2) to (9) were measured under the same conditions.

Table 2

| | Example 1<br>Compound (1) | Example 2<br>Compound (2) | Example 3<br>Compound (3) |
|---|---|---|---|
| Structural<br>Formula | (structure) | (structure) | (structure) |
| Oxidation<br>potential | None | None | None |

Table 2-continued

| | Example 4 Compound (4) | Comparative Example 1 Compound (5) | Comparative Example 2 Compound (6) |
|---|---|---|---|
| Structural Formula | | | |
| Oxidation potential | None | None | None |

| | Comparative Example 3 Compound (7) | Comparative Example 4 Compound (8) | Comparative Example 5 Compound (9) |
|---|---|---|---|
| Structural Formula | | | |
| Oxidation potential | None | 0.65 V<br>1.00 V<br>1.15 V | 1.14 V |

From the results shown in Table 2, it was found that, as shown in Comparative Examples 4 and 5, the oxidation potential was observed in a case where the benzene ring at the 3-position of benzofuranone had a hydroxyl group. That is, it was shown that the lactone compound was oxidatively decomposed, and it was shown that the water stability under applied voltage was low.

From the results shown in Tables 1 and 2, it was found that all of the compounds (1) to (4), which correspond to the lactone compound represented by Formula (I) described above, were excellent in water stability over time without applied voltage and water stability under applied voltage.

What is claimed is:

1. A lactone compound represented by Formula (I),

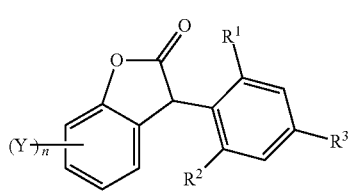

(I)

here, in Formula (I),
$R^1$ and $R^2$ each independently represent an alkyl group or an alkoxy group,
$R^3$ represents an alkyl group or an alkoxy group,
Y represents an alkyl group and n represents an integer of 1 to 4, and in a case where n is an integer of 2 to 4, a plurality of Y's may be the same substituent or substituents different from each other, and at least one of Y's is tert-butyl.

2. The lactone compound according to claim 1, wherein $R^1$ to $R^3$ in Formula (I) represent the same substituent.

3. The lactone compound according to claim 1, wherein Y in Formula (I) represents a substituent having 3 or more carbon atoms.

4. The lactone compound according to claim 1, wherein the lactone compound is represented by any of Formulae (1) to (4),

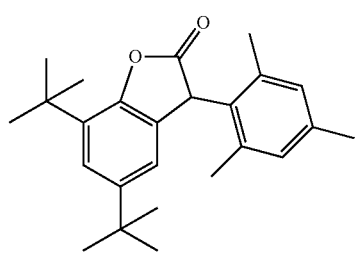 [SMILES: Cc1cc(C)c(C2C(=O)Oc3c2cc(C(C)(C)C)cc3C(C)(C)C)c(C)c1]

(1)

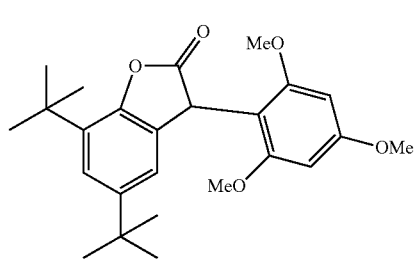

(2)

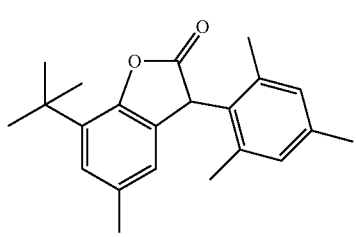
(3)
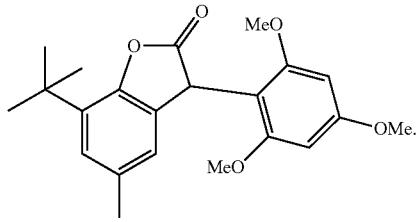
(4)
* * * * *